(12) United States Patent
Reardan et al.

(10) Patent No.: US 7,553,863 B2
(45) Date of Patent: Jun. 30, 2009

(54) ULTRAPURE 4-METHYLPYRAZOLE

(75) Inventors: Dayton T. Reardan, Shorewood, MN (US); Michel D. Combe, Fox Point, WI (US)

(73) Assignee: Paladin Labs (Barbados) Inc., Barbados (BB)

( * ) Notice: Subject to any disclaimer, the term of this patent is extended or adjusted under 35 U.S.C. 154(b) by 416 days.

(21) Appl. No.: 11/279,708

(22) Filed: Apr. 13, 2006

(65) Prior Publication Data

US 2007/0244330 A1 Oct. 18, 2007

Related U.S. Application Data

(60) Provisional application No. 60/776,009, filed on Apr. 21, 2005.

(51) Int. Cl.
*A61K 31/415* (2006.01)
*C07D 231/12* (2006.01)

(52) U.S. Cl. .................... 514/403; 548/356.1

(58) Field of Classification Search ............... 514/403; 548/356.1
See application file for complete search history.

(56) References Cited

U.S. PATENT DOCUMENTS

| | | | |
|---|---|---|---|
| 1,442,520 A | 1/1923 | Buc | |
| 1,879,210 A | 9/1932 | Hahl | |
| 2,380,524 A | 7/1945 | Hillyer | |
| 2,482,725 A | 9/1949 | Bramwyche | |
| 2,515,160 A | 7/1950 | Copenhaver | |
| 2,667,517 A | 1/1954 | Longley, Jr. | |
| 2,842,576 A | 7/1958 | Habeshaw et al. | |
| 2,962,534 A | 11/1960 | Montagna et al. | |
| 3,021,373 A | 2/1962 | Montagna et al. | |
| 3,218,359 A | 11/1965 | Aguadisch | |
| 3,296,314 A | 1/1967 | Burns et al. | |
| 3,846,088 A | 11/1974 | Brown et al. | |
| 4,209,643 A | 6/1980 | Shin | |
| 5,128,480 A | 7/1992 | Merkle et al. | |
| 5,354,911 A | 10/1994 | Weber et al. | |
| 5,569,769 A | 10/1996 | Merkle et al. | |
| 5,576,465 A | 11/1996 | Kaufhold | |
| 5,792,876 A | 8/1998 | Iwasaki et al. | |
| 6,229,022 B1 | 5/2001 | Merkle et al. | |
| 6,313,322 B1 | 11/2001 | Hieber et al. | |
| 2004/0024260 A1 | 2/2004 | Winkler et al. | |

FOREIGN PATENT DOCUMENTS

| | | |
|---|---|---|
| EP | 0366328 A1 | 5/1990 |
| EP | 0366328 A1 * | 5/1990 |
| EP | 490221 B1 | 8/1995 |
| WO | WO-2006115626 A2 | 11/2006 |
| WO | WO-2006115626 A3 | 11/2006 |

OTHER PUBLICATIONS

"Ethyl propenyl ether, mixture of cis- and trans- isomers", *ChemExper chemical dictionary—Catalog of chemicals and suppliers* (http://chemeth.chemexper.com), (searched Apr. 2005),3 pgs.

"Severe Ethylene Glycol Ingestion Treated Without Hemodialysis", *Pediatrics 107*(1), (Jan. 2001),172-173.

Eisses, Karel T., "Differences in Teratogenic and Toxic Properties of Alcohol Dehydrogenase Inhibitors Pyrazole and 4-Methylpyrazole in Drosophila melanogaster: I. ADH Allozymes in Variable Genetic Backgrounds", *Teratogenesis, Carcinogenesis, and Mutagenesis 15*, (1995),1-10.

"Search Report and Written Opinion for International Application No. PCT US2006 009979", Feb. 10, 2006 (Date mailed).

Yanovskaya, L. A., et al., "Chemistry of Acetals, I. A General Method of Synthesis of Tetraethyl Acetals of Beta-Dicarbonyl compounds", *N.D. Zelinskii Inst. Org. Chem.*, Moscow, Izvestiya Akademii Nauk SSSR, Seriya Khimicheskaya, (1960), 1246-53.

* cited by examiner

*Primary Examiner*—Rei-Tsang Shiao
*Assistant Examiner*—Janet L Coppins
(74) *Attorney, Agent, or Firm*—Schwegman, Lundberg & Woessner, P.A.

(57) ABSTRACT

Disclosed is an ultrapure 4-methylpyrazole containing less than 0.1% pyrazole and containing less than 10 ppm each of hydrazine and nitrobenzaldehyde. The ultrapure 4-methylpyrazole is prepared by a novel process so that less than 0.01% of ethylvinyl ether is present.

16 Claims, No Drawings

ULTRAPURE 4-METHYLPYRAZOLE

CROSS-REFERENCE TO RELATED APPLICATIONS

This application claims the benefit of priority, under 35 U.S.C. 119(e), to U.S. Provisional Application Ser. No. 60/776,009, filed Apr. 21, 2005, titled "ULTRAPURE 4-METHYLPYRAZOLE," which is herein incorporated by reference.

FIELD OF THE INVENTION

The present invention relates to ultrapure 4-methylpyrazole containing extraordinarily low levels of pyrazole, hydrazine, and nitrobenzaldehyde impurities and to a novel synthesis thereof.

BACKGROUND OF THE INVENTION

Ethylene glycol is commonly available as automobile radiator antifreeze. Because of its sweet taste, improperly stored antifreeze is a common source of ethylene glycol poisoning, particularly in children. Ethylene glycol is rapidly absorbed from the gastrointestinal tract. Toxicity can be divided into three stages:
Stage 1—Neurological (0.5-12 hours post-ingestion)
Stage 2—Cardiopulmonary (12-24 hours post-ingestion)
Stage 3—Renal (24-72 hours post-ingestion)

4-Methylpyrazole, marketed as Antizol® (fomepizole) by Orphan Medical, Inc. is a specific antidote for the treatment of ethylene glycol poisoning. It works by inhibiting the enzyme alcohol dehydrogenase which is responsible for the conversion of ethylene glycol, which itself is relatively non-toxic, into its toxic metabolites that in turn cause the renal injury and metabolic acidosis. Antizol® is currently approved by the FDA as an antidote for ethylene glycol poisoning or suspected ethylene glycol poisoning and is recommended by poison control centers as first line therapy. See Antizol® (fomepizole) Injection, Product Monograph, Orphan Medical, Inc., 2001, the entire contents of which are hereby incorporated by reference.

Methanol is commonly available in the home in automobile windshield washer fluid and as a gas line anti-icing additive. Methanol has a minor degree of direct toxicity. Its major toxicity follows its metabolism to formic acid. Antizol® is also a specific antidote for the treatment of methanol toxicity. It works by inhibiting the enzyme alcohol dehydrogenase which is responsible for the conversion of methanol into its toxic metabolites, formaldehyde and formic acid. Again, Antizol® is approved by the FDA for use in treating methanol poisoning or suspected methanol poisoning and is recommended by poison control centers as first line therapy.

Known methods of preparing 4-methylpyrazole include the reaction of alpha, beta-unsaturated carbonyl compounds or diketones with hydrazine or hydrazine derivatives or the dehydrogenation of the corresponding 2-pyrazoline. See U.S. Pat. Nos. 3,200,128, 4,996,327, and 5,569,769. Other processes for preparing 4-methylpyrazole are disclosed in U.S. Pat. Nos. 6,229,022, 5,569,769, and 4,996,327.

4-methylpyrazole prepared by synthetic routes employed heretofore may contain impurities and toxic by-products, including pyrazole, hydrazine, and nitrobenzaldehyde. Pyrazole, like 4-methylpyrazole, is also an inhibitor of alcohol dehydrogenase, but is more toxic than 4-methylpyrazole. Pyrazole is a known teratogen (Eisses, 1995) with 10 fold less potency against alcohol dehydrogenase (T. Li et al., *Acta Chem. Scan.* 1969, 23, 892-902). In addition, Ewen MacDonald published a paper in 1976 that showed pyrazole in contrast to 4-methylpyrazole has a detrimental effect on brain levels of noradrenaline (E. MacDonald, *Acta Pharmacol. et Toxicol.* 1976, 39, 513-524). Hydrazine and nitrobenzaldehyde are known mutagens and carcinogens (H. Kohno et al., *Cancer Sci.* 2005, 96, 69-76).

These impurities and toxic by-products have been tolerated heretofore because methods of making ultrapure 4-methylpyrazole have not been available. The FDA has previously approved up to 0.5% pyrazole in Antizol®, but recently is requesting a higher level of purity of less than 0.1% pyrazole to qualify such high levels with animal and other studies. Therefore, while the purity of Antizol® is sufficiently high for its antidotal use in emergency medicine, such toxic impurities are not ideal. For example a pregnant woman who needs antidote therapy would risk exposure of a fetus to potentially toxic pyrazole of known teratogenicity and potentially high levels of known carcinogens. Therefore, a need exists for a 4-methylpyrzaole with even lower amounts of pyrazole and other impurities and for a synthesis of such an ultrapure 4-methylpyrazole.

SUMMARY OF THE INVENTION

The present invention provides 4-methylpyrazole (4-MP) containing less than 0.1% pyrazole.

The present invention further provides 4-methylpyrazole containing less than 10 ppm each of hydrazine and nitrobenzaldehyde.

The present invention also provides a novel process for making 4-methylpyrazole containing less than 0.1% pyrazole and less than 10 ppm each of hydrazine and nitrobenzaldehyde. The novel process includes a step for producing 1-ethoxy-1-propene under controlled reaction conditions and work-up conditions to produce 1-ethoxy-1-propene that is substantially free of ethylvinyl ether,

DETAILED DESCRIPTION OF THE INVENTION

The present invention provides a novel five-step process of making 4-methylpyrazole that results in less than 0.1% pyrazole and less than 10 ppm each of hydrazine and nitrobenzaldehyde in the final product.

The term "about" is intended to encompass variations in parameters or in amounts of ingredients owing to variations in weighing and other measurement techniques, purity of ingredients, and the like, as would be known to the art worker. Such variations are usually no more than about ±0.5%.

In the first step of the present synthesis of 4-MP, propionaldehyde is reacted with triethyl orthoformate in the presence of ethanol and ammonium nitrate to produce 1,1-diethoxypropane. In the second step, the 1,1-diethoxypropane produced in the first step is reacted neat (without a solvent) with a catalyst, which comprises an acid and an amine, to produce 1-ethoxy-1-propene (ethyl-1-propenyl ether). In the third step, this material is purified by washing and drying, without distillation. In the fourth step, the 1-ethoxy-1-propene from the third step is reacted with triethyl orthoformate in the presence of boron trifluoride-diethyl etherate to produce 1,1,3,3-tetraethoxy-2-methyl propane ("TEMP"). In the fifth step, the TEMP from the third step is reacted with hydrazine or a hydrazonium salt or hydrazine hydrate at elevated temperatures to produce 4-methylpyrazole.

In the second step, the acid requirement is very low; typically 0.00015 to 0.008, including 0.0002 to 0.006, for example 0.00025 to 0.0015 mol of acid is employed per mol of 1,1-diethoxypropane. The acid selected typically has a pK of $\leq 2.5$, including $\leq 2.2$, for example $\leq 2.0$.

Suitable acids include phosphoric acid, its partially esterified derivatives, sulfuric acid, sulfuric acid hemiesters, and aliphatic or aromatic sulfonic acids. Aromatic sulfonic acids, such as benzenesulfonic acid and toluenesulfonic acid are especially suitable, and p-toluenesulfonic acid, has proven to be highly suitable.

The amine in the second step is used in certain amount ratios vis-à-vis the acid. Typical acid:amine ratios include about 1:0.4-0.6. A particularly suitable molar ratio of acid to amine is about 1:0.5

The amine and acid catalyst component should not be volatile under the reaction conditions. Accordingly, the amine and acid should have a boiling point which is at least 10° C., typically at least 20° C., for example 30° C., above the boiling points of the reaction products formed. Primary, secondary, and/or tertiary aliphatic, cycloaliphatic, and aromatic amines may be used, including nitrogen-containing heterocyclic compounds, such as pyridines, piperidines, or quinolines.

Suitable aliphatic amines include straight-chain and/or branched aliphatic amines. Examples of amines include n-octyl, n-nonyl, n-decyl-, n-dodecyl-, 2-ethylhexyl-, i-nonyl-, 3,5,5-trimethylhexyl-, di-n-butyl-, di-1-butyl-, di-amyl-, di-n-hexyl-, di-n-octyl-, di-2-ethylhexyl-, di-1-nonyl-, tri-n-propyl-, tri-n-butyl-, tri-n-pentyl-, tri-n-hexyl-, tri-n-octyl-, tri-2-ethylhexyl-, tri-n-nonyl-, tri-1-nonyl- and tri-n-decylamine. Isononylamine, diamylamine, tri-n-butylamine, bis(2-ethylhexyl)amine, and diisononylamine have proven particularly useful as the amine.

In the fourth step, boron trifluoride-diethyl etherate ($Et_2O.BF_3$) acts as a catalyst. Accordingly, it is employed in catalytic, rather than in stoichiometric amounts.

In the fifth step, hydrazine, hydrazine hydrate, or a hydrazonium salt preferably should remain soluble in the reaction mixture to avoid losses of yield owing to incomplete reaction. For this reason, a hydrazonium salt is typically used. Suitable hydrazonium salts include the hydrazonium halides (fluoride, chloride, or iodide) and hydrazine hydrosulfate. Elevated temperatures employed typically are about 70-85° C., including about 80-85° C., for example about 80° C.

The process of the present invention is set forth in the following exemplary scheme:

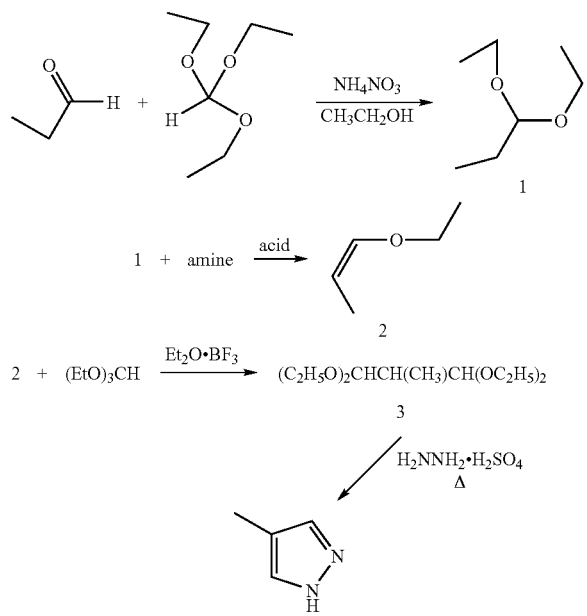

The process of the present invention can be carried out both batchwise and continuously. An important aspect of the above synthetic scheme is the high level of purity of the 1-ethoxy-1-propene 2 achieved before the reaction thereof with triethyl orthoformate in the fourth step to produce 3. The presence of ethylvinyl ether side product in 2 will lead to the undesired presence of pyrazole in the final product. Commercially available 1-ethoxy-1-propene cannot be used in the present process because the level of ethylvinyl ether therein is too high.

The process of the present invention results in Compound 2 containing less than 0.01% ethylvinyl ether that can result in pyrazole formation under the conditions of the fourth step. This is accomplished by controlling the reaction conditions and work-up procedure in the second step as follows: the molar ratio of acid to amine is controlled to about 1:0.4-0.6, a low reaction temperature (about 140 to 160° C.) is used, the product is washed with water and not distilled. The organic layer is dried over a drying agent such as magnesium sulfate or Drierite.

The presence of less than 0.01% ethylinyl ether in 2, and less than 0.1% pyrazole and less than 10 ppm of hydrazine in the final product can be confirmed via a gas chromatographic system that allows for detection of the content of ethylvinyl ether below a level of 0.01% relative to 1-ethoxy-1-propene and that allows for detection of pyrazole below a level of 0.1% relative to 4-methylpyrzaole. A suitable gas chromatographic (GC) system has the following components (equivalents of the recited components may also be used):

a Hewlett Packard Model 5890 Series II gas chromatograph; a Hewlett Packard Model 18596C sample tray; a Hewlett Packard 1-100 ml flowmeter; a Hewlett Packard VL18DT GC computer with Hewlett Packard ChemStation software installed therein; a Hewlett Packard Model 18593B GC auto-sampler; a flame ionization detector; an Alltech 6'×⅛' 10% Carbowax 80/100 GC column; Hewlett Packard Model C#5182-0544 GC sample vials; and a Branson Model 200 sonicator. Compressed air, helium gas, and hydrogen gas are all UHP grade and 99.999% pure.

Column temperatures typically may be from 33° C. to 37° C. Retention times are very sensitive to helium flow and column head pressure. Exemplary ranges of suitable retention times (in minutes) determined with authentic samples are as follows: ethylvinyl ether: 2.781-2.788; trans-1-ethoxy-1-propene: 4.883-4.899; and cis-1-ethoxy-1-propene: 5.776-5.794.

The above system has a limit of detection of 0.0001% ethylvinyl ether and a limit of quantitation of 0.0003% of ethylvinyl ether, both relative to a 1.0 μl nominal injection volume of 1-ethoxy-1-propene.

The process of the present invention results in 4-methylpyrazole containing less than 0.1% pyrazole and less than 10 ppm each of hydrazine or nitrobenzaldehyde. This low hydrazine content is achieved by using a slight molar excess of TEMP in step five. A slight molar excess typically is about 0.1% to about 0.5%. Because the level of hydrazine is so low, there is no need to add a nitrobenzaldehyde, such as p-nitrobenzaldehyde, to derivatize, and thus to remove, the unreacted hydrazine. Accordingly, no measurable nitrobenzaldehyde is present in the final product.

The invention will now be illustrated by the following non-limiting examples:

EXAMPLE 1

Preparation of 1,1-diethoxypropane 1

Into a 2-liter flask under nitrogen were added 586 g (3.96 moles) of triethyl orthoformate, 46 g (56 ml, 1 mole) of ethanol, and 16 g of ammonium nitrate. Over the course of one hour 232 g (4 moles) of propionaldehyde were added with stirring. An ice bath was used as necessary to keep maintain the mixture at 30-36° C. The mixture turned yellow orange after one-third of the propionaldehyde had been added. The mixture was stirred overnight at room temperature and then brought to pH 7.5±0.2 with 10% aqueous sodium carbonate (about 30 ml). The aqueous layer was decanted, and the organic layer was distilled over sodium carbonate at atmospheric pressure to produce 124 g (81.6%) of 1.

EXAMPLE 2

Preparation of 1-ethoxy-1-propene 2

Into a 500 ml flask equipped with a 12"×¾" packed column were added 0.25 g (0.0013 moles) of p-toluene sulfonic acid, followed by 241 g (1.82 moles) of 1. Nitrogen was bubbled into the mixture while 0.157 g (0.00065 moles) of bis(2-ethylhexyl)amine were added. The nitrogen flow was reduced, and the mixture was distilled to 160° C. to partially remove ethyl alcohol and 1-ethoxy-1-propene. The reaction mixture washed with 320 ml of water and then with 70 ml of water. The organic layer was dried over magnesium sulfate and filtered to produce 121 g (77.5%) of 2, bp 67-76° C., as a clear, colorless liquid. Gas chromatographic analysis showed less than 0.01% ethylvinyl ether.

EXAMPLE 3

Preparation of 1,1,3,3-tetraethoxy-2-methylpropane 3

Into a 5 liter flask equipped with a mechanical stirrer were added 790 g (5.34 moles) of triethyl orthoformate and 4.28 ml of boron trifluoride-diethyl etherate under a nitrogen atmosphere. Temperature was maintained at 25° C. with cooling as needed. To this mixture were added 230 g (2.67 moles) of 1-ethoxy-1-propene were added slowly and dropwise. The reaction mixture was exothermic; the temperature rose to about 35-38° C. The pot was cooled to 25° C. and stirring was continued for one hour. Solid anhydrous sodium carbonate (32.1 g, 0.3 moles) was added in one portion to the flask and stirring was continued for one hour. The mixture was filtered and the filtrate was fractionally distilled under reduced pressure. The light fraction was removed at a pot temperature of 55-60° C. at 10 mm pressure. The vacuum was improved to 3 mm and the pot temperature was permitted to rise to about 100-140° C. to produce 500 g (80%) of 3, bp 80-81° C. at 3 mm, as a clear, colorless to yellow-brown liquid.

EXAMPLE 4

Preparation of 4-methylpyrazole

Into a 5 liter flask equipped with a mechanical stirrer were added 1750 ml of sterile USP water to which 266.7 g (2.05 moles) of hydrazine hydrosulfate were added gradually over one hour with stirring. To the above mixture was added dropwise 481 g (2.053 moles) of 3 and the reaction mixture was warmed to 80° C. Heating and stirring were maintained for 3 hours, the flask was cooled to 40° C., and the volatile components were distilled off under a reduced pressure of about 125 mm. The resulting mixture was cooled to 10° C. first with water and then with glycol; 20 ml of water were added to the flask, and cooling was continued to a temperature of 3° C. Thereafter 50% sodium hydroxide solution was added with cooling so as to maintain the temperature below 30° C. The pH of the reaction mixture should be between 4 and 6. A solution of sodium bicarbonate containing 4.9 g of sodium bicarbonate to 55 ml of water was added to the flask. Additional sodium bicarbonate solution was added until the pH reached 7.0. The flask temperature was allowed to rise to 27° C. with continued stirring. The contents of the flask were extracted with ethyl acetate and the aqueous layer was separated. The organic layer was dried over magnesium sulfate, filtered, and the extract was distilled under vacuum. The light fraction was removed at a pot temperature of 55-60° C. at 125 mm pressure. The vacuum was improved to 5 mm for the remainder of the distillation; pot temperatures were permitted to rise to 100-110° C. to produce 134.8 g (84% based on 3) of 4-methylpyrazole, bp 77-80° C. at 5 mm, as a clear, colorless to yellow liquid. Gas chromatographic analysis showed less than 0.1% pyrazole and less than 10 ppm hydrazine.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to incorporate physically into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention.

The invention described illustratively herein suitably may be practiced in the absence of any element or elements, or limitation or limitations, which is not specifically disclosed herein as essential. The methods and processes described illustratively herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "the 4-methylpyrazole" includes a plurality of such 4-methylpyrazoles, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also forms part of the invention. This includes the generic description of the invention with a proviso or negative limitation removing any subject matter from the genus, regardless of whether or not the excised material is specifically recited herein.

What is claimed is:

1. A solution containing 4-methyl pyrazole containing less than 0.1% pyrazole.

2. The solution of claim 1 containing less than 10 ppm each of hydrazine and nitrobenzaldehyde.

3. The solution of claim 2, wherein the nitrobenzaldehyde is p-nitrobenzaldehyde.

4. A process of making 4-methylpyrazole containing less than 0.1% pyrazole comprising the steps:
   (a) reacting propionaldehyde with triethyl orthoformate to produce 1,1-diethoxypropane;
   (b) reacting the 1,1-diethoxypropane of step (a) with an amine and an acid at a temperature of about 140-160° C. to produce 1-ethoxy-1-propene;
   (c) washing the 1-ethoxy-1-propene with water and drying it without distillation;
   (d) reacting the dried 1-ethoxy-1-propene of step (c) with triethyl orthoformate in the presence of a catalytic amount of boron trifluoride-diethyl etherate to produce 1,1,3,3-tetraethoxy-2-methylpropane; and
   (e) reacting the 1,1,3,3-tetraethoxy-2-methylpropane of step (d) with hydrazine or a hydrazonium salt to produce 4-methylpyrazole containing less than 0.1% pyrazole.

5. A process of making 4-methylpyrazole containing less than 0.1% pyrazole and less than 10 ppm each of hydrazine and nitrobenzaldehyde comprising the steps:
   (a) reacting propionaldehyde with triethyl orthoformate to produce 1,1-diethoxypropane;
   (b) reacting the 1,1-diethoxypropane of step (a) with an amine and an acid at a temperature of about 140-160° C. to produce 1-ethoxy-1-propene;
   (c) washing the 1-ethoxy-1-propene with water and drying it without distillation;
   (d) reacting the dried 1-ethoxy-1-propene of step (c) with triethyl orthoformate in the presence of a catalytic amount of boron trifluoride-diethyl etherate to produce 1,1,3,3-tetraethoxy-2-methylpropane; and
   (e) reacting the 1,1,3,3-tetraethoxy-2-methylpropane of step (d) with hydrazine or a hydrazonium salt to produce 4-methylpyrazole containing less than 0.1% pyrazole and less than 10 ppm each of hydrazine and nitrobenzaldehyde.

6. The process of claim 4 or 5 wherein the molar ratio of acid to amine is about 1:0.4-0.6.

7. The process of claim 6 wherein the reaction temperature is about 160° C.

8. The process of claim 4 or 5 wherein the 1-ethoxy-1-propene of step (b) is dried over a drying agent in step (c).

9. The process of claim 8 wherein the drying agent is magnesium sulfate.

10. The process of claim 4 or 5 wherein the dried 1-ethoxy-1-propene of step (c) contains less than 0.01% ethylvinyl ether.

11. The process of claim 10 wherein less than 0.01% ethylvinyl ether is present in the dried 1-ethoxy-1-propene of step (c) as a result of the molar ratio of acid to amine, the reaction temperature, and the washing and drying of the product without distillation.

12. The process of claim 4 or 5 wherein in step (e) a slight molar excess of 1,1,3,3-tetraethoxy-2-methylpropane is used relative to the hydrazine or hydrazonium salt.

13. The process of claim 12 wherein the molar excess is about 0.1% to about 0.5%.

14. The process of any one of claims 4, 5 or 12 wherein a hydrazonium salt is used in step (e).

15. The process of claim 14 wherein the hydrazonium salt is hydrazine hydrosulfate.

16. A composition consisting essentially of 4-methyl pyrazole containing less than 0.1% pyrazole.

* * * * *

UNITED STATES PATENT AND TRADEMARK OFFICE
CERTIFICATE OF CORRECTION

| | |
|---|---|
| PATENT NO. | : 7,553,863 B2 |
| APPLICATION NO. | : 11/279708 |
| DATED | : June 30, 2009 |
| INVENTOR(S) | : Dayton T. Reardan et al. |

It is certified that error appears in the above-identified patent and that said Letters Patent is hereby corrected as shown below:

In column 2, line 16, delete "4-methylpyrzaole" and insert -- 4-methylpyrazole --, therefor.

In column 2, line 33, delete "ether," and insert -- ether. --, therefor.

In column 3, line 7, after "1:0.5" insert -- . --.

In column 3, line 18, delete "di-1-butyl-," and insert -- di-i-butyl-, --, therefor.

In column 3, line 19, delete "di-1-nonyl-," and insert -- di-i-nonyl-, --, therefor.

In column 3, line 21, delete "tri-1-nonyl-" and insert -- tri-i-nonyl- --, therefor.

In column 3, line 26, delete "(Et$_2$O.BF$_3$)" and insert -- (Et$_2$O·BF$_3$) --, therefor.

In column 4, line 16, delete "ethylinyl" and insert -- ethylvinyl --, therefor.

In column 4, line 22, delete "4-methylpyrzaole." and insert -- 4-methylpyrazole. --, therefor.

In column 5, line 20, delete "washed" and insert -- was washed --, therefor.

Signed and Sealed this

Sixth Day of October, 2009

David J. Kappos
*Director of the United States Patent and Trademark Office*